US008697671B2

(12) United States Patent
Karageozian et al.

(10) Patent No.: US 8,697,671 B2
(45) Date of Patent: *Apr. 15, 2014

(54) STABILIZED GLYCOSAMINOGLYCAN PREPARATIONS AND RELATED METHODS

(71) Applicant: S.K. Pharmaceuticals, San Juan Capistrano, CA (US)

(72) Inventors: Hampar L. Karageozian, San Juan Capistrano, CA (US); John Y. Park, Santa Ana, CA (US)

(73) Assignee: S.K. Pharmaceuticals, Inc., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,037

(22) Filed: Oct. 9, 2012

(65) Prior Publication Data

US 2013/0102561 A1  Apr. 25, 2013

Related U.S. Application Data

(60) Division of application No. 11/940,171, filed on Nov. 14, 2007, now Pat. No. 8,288,362, which is a continuation-in-part of application No. 11/126,075, filed on May 9, 2005, now Pat. No. 7,544,671.

(60) Provisional application No. 60/569,407, filed on May 7, 2004.

(51) Int. Cl.
*A01N 43/04* (2006.01)
*A61K 31/70* (2006.01)

(52) U.S. Cl.
USPC ................................... 514/54; 514/23; 514/62

(58) Field of Classification Search
None
See application file for complete search history.

(56) References Cited

U.S. PATENT DOCUMENTS

| | | | |
|---|---|---|---|
| 5,073,545 A | 12/1991 | Arima et al. | |
| 5,141,741 A | 8/1992 | Ishida et al. | |
| 5,273,056 A | 12/1993 | McLaughlin et al. | |
| 5,633,001 A * | 5/1997 | Agerup | 424/423 |
| 5,846,228 A | 12/1998 | Alexander | |
| 6,372,755 B2 | 4/2002 | Hanamura et al. | |
| 2002/0127196 A1 | 9/2002 | Avila et al. | |
| 2004/0137079 A1 | 7/2004 | Cook et al. | |
| 2004/0191284 A1 | 9/2004 | Yu et al. | |
| 2005/0152948 A1 | 7/2005 | Hunter et al. | |
| 2006/0204471 A1 | 9/2006 | Lacharriere et al. | |
| 2006/0258698 A1 | 11/2006 | Mudumba et al. | |

FOREIGN PATENT DOCUMENTS

| | | |
|---|---|---|
| EP | 0 705 095 B1 | 11/1997 |
| GB | 2160097 A | 12/1985 |
| JP | 5170641 A | 7/1993 |
| JP | 92-27385 A | 9/1997 |
| JP | 10-72376 A | 3/1998 |
| JP | 10-290830 A | 11/1998 |
| JP | 2001-19611 A | 1/2001 |
| JP | 2002-193815 A | 7/2002 |
| JP | 2002-370966 A | 12/2002 |
| JP | 2003-530136 A | 10/2003 |
| JP | 2003-342197 A | 12/2003 |
| WO | WO00/59516 A1 | 10/2000 |
| WO | WO03/061626 A1 | 7/2003 |

OTHER PUBLICATIONS

Gutowska et al. The Anatomical record (2001), vol. 263, pp. 342-349.*
Lindenhayn et al. J. Biomed. Mater. Res. (1999), vol. 44, pp. 149-155.*
Steckel et al., International Journal of Pharmaceutics (2003), vol. 257, pp. 181-194.
USPTO Office Action dated Jul. 23, 2008 in related U.S. Appl. No. 11/126,075 filed May 9, 2005, now U.S. Patent 7,544,671.
USPTO Office Action dated Aug. 21, 2007 in related U.S. Appl. No. 11/126,075 filed May 9, 2005, now U.S. Patent 7,544,671.
Lindenhayn et al. Journal of Biomedical Materials Research (1999), vol. 44, pp. 149-155.

* cited by examiner

*Primary Examiner* — Patrick Lewis
(74) *Attorney, Agent, or Firm* — Robert D. Buyan; Stout, Uxa, Buyan & Mullins, LLP

(57) ABSTRACT

Compositions comprising a glycosaminoglycan (e.g., a hyaluronan, hyaluronic acid, hyaluronate, sodium hyaluronate, dermatan sulfate, karatan sulfate, chondroitin 6-sulfate, heparin, etc.) in combination with at least one component selected from; i) polyglycols (e.g., polyethylene glycol), ii) long chain hydroxy polyanionic polysaccharides (e.g., dextran, sodium alginate, alginic acid, propylene glycol alginate, carboxymethyl cellulose and carboxyethyl cellulose, hydroxyl ethyl starch, hydroxyl propyl methyl cellulose, hydroxy propyl ethyl cellulose, hydroxy propyl cellulose, methyl cellulose, polylysine, polyhistidine, polyhydroxy proline, poly ornithine, polyvinyl pyrolidone, polyvinyl alcohol, chitosan, etc.) and iii) long chain Nitrogen containing polymers (e.g., Polylysine, Polyvinylpyrrolidone, and polyvinyl alcohol). The invention also includes methods for using such compositions (e.g., as substance delivery materials, tissue fillers or bulking agents, as moistening or hydrating agents, etc.).

22 Claims, 4 Drawing Sheets

STABILIZED GLYCOSAMINOGLYCAN PREPARATIONS AND RELATED METHODS

RELATED APPLICATION

This application is a division of U.S. patent application Ser. No. 11/940,171 filed Nov. 14, 2007 and issuing on Oct. 16, 2012 as U.S. Pat. No. 8,288,362, which is a continuation in part of U.S. patent application Ser. No. 11/126,075 filed May 9, 2005 and issued as U.S. Pat. No. 7,544,671, which claims priority to U.S. Provisional Patent Application No. 60/569,407 filed on May 7, 2004, the entire disclosures of each such earlier-filed application being expressly incorporated herein by reference.

FIELD OF THE INVENTION

The present invention relates generally to the fields of chemistry, pharmaceutical formulation and medicine and more particularly to stabilized glycosaminoglycan compositions and their methods of manufacture and use.

BACKGROUND OF THE INVENTION

Hyaluronan is part of a group of polysaccharides known as glycosaminoglycans. In particular, hyaluronan is a mucopolysaccharide that occurs naturally in the bodies of humans and other animals. The term hyaluronan encompasses hyaluronic acid as well as salts of hyaluronic acid, such as sodium hyaluronate. The term hyaluronate refers to the conjugate base of hyaluronic acid. Hyaluronan is the polyanionic form of hyaluronic acid, which exists in vivo.

In general, glycosaminoglycans are made up of repeating disaccharide units containing a derivative of an aminosugar. The repeating disaccharide unit of hyaluronan consists of alternating glucuronic acid and N-acetylglucosamine units, which are repeated over and over to form long chains. Each repeating disaccharide unit has one carboxylate group, four hydroxyl groups, and an acetamido group. Hyaluronan differs from the other major glycosaminoglycans in that it does not have sulfate groups. The chemical structure of hyaluronan is as follows:

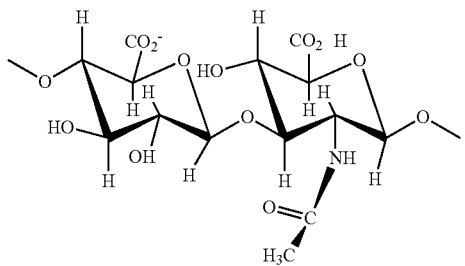

Hyaluronan in the extracellular matrix of various body tissues. In normal physiological states hyaluronan molecules form random coils in the nature of helical ribbons that are stiffened by hydrogen bonds and solvent interactions. The axial hydrogen atoms are relatively non-polar while the equatorial side chains are relatively polar, thereby creating the twisting ribbon structure.

Hyaluronan is synthesized in the body by many types of cells and tends to collect in extracellular spaces where acts as a scaffold for aggrecan self-assembly, thereby combining with other constituents to form supportive or protective networks around the cells. Hyaluronan is present in many body fluids and tissues and is found in relatively high concentrations in vitreous humor and synovial fluid.

Hyaluronan is highly lubricious, hydrophilic and exhibits unique rheological properties. The unique rheology of hyaluronan is believed to be due at least in part to the fact that the hyaluronan polymer coils become entangled with each other at low concentrations and exhibit shear-dependent viscosity at high concentrations. For example, a 1% solution of hyaluronan may exist as a gelatinous mass under ambient conditions but, when compressed, will become less viscous and easily flowable such that it may be injected through a hypodermic needle. Because of this unique rheological behavior, hyaluronan has been referred to as a "pseudo-plastic" material. The hydrophilic nature of hyaluronan is believed to be a function of the fact that hyaluronan forms stiffened helical ribbons as described above. Each such helical ribbon is configured such that it may trap substantial amounts of water (e.g., approximately 1000 times its weight in water).

Hyaluronan has a wide variety of medical and non-medical applications. For example, hyaluronan solutions make excellent lubricants and may allow tissue surfaces to slide over one another. Thus, hyaluronan preparations are sometimes applied to tissues to promote healing and/or to reduce the potential for postoperative adhesion formation. One of its important biological roles is to provide beneficial effects on wound healing in the skin and eyes.

Recently, hyaluronan has been found to enhance corneal epithelial healing and corneal reepithelialization for non-infectious corneal erosion. These beneficial effects can be extended to the management of dry eye syndrome, allergic conjunctivitis, and contact lens wear.

For example, dry eye is a syndrome in which inadequate tear production and inappropriate tear composition causes the cornea and conjunctiva improper wetting. Untreated dry eye can be further deteriorated to produce more severe epithelial erosion, strands of epithelial cells, dry spots on the cornea. These can be complicated further by microbial infection. Thus, an early medical management for the dry eye syndrome would be highly desirable. Such an early treatment of the dryness and irritation of the eye by the use of hyaluronan could be very effective and beneficial medical management of the dry eye.

Additionally, it has been known for a long time that contact lenses which have adsorption of cellular debris, mucus materials, lipids and proteins from the eye can cause irritation and/or infection of the eye. Thus, a biocompatible lubricant, particularly hyaluronan can provide beneficial effects to prevent the deposit from forming in its early stage of deposit formation on the contact lenses in the eye.

As indicated above, beneficial effects of hyaluronan for the health of the eye are great; however, use of hyaluronan has been rather limited due to its chemical instability losing its viscosity and lubricity in aqueous solution.

The prior art has included a number of stabilized hyaluronic acid gels useable for cosmetic tissue bulking. For example, RESTALYNE® Injectable Gel; (Medicis Pharmaceutical Corporation, Scottsdale, Ariz.) is a sterile gel of stabilized sodium hyaluronate. Also, PERLANE® injectable gel (Medicis Pharmaceutical Corporation, Scottsdale, Ariz.) is a sterile gel of hyaluronic acid chemically cross-linked with BDDE, stabilized and suspended in phosphate buffered saline at pH=7 and concentration of 20 mg/mL.

Additionally, the prior art has included a number of hyaluronic acid containing viscoelastic preparations used in cataract surgery. For example, VISCOAT® viscoelastic solution (Alcon) contains purified medium molecular weight sodium chondroitin sulfate and sodium hyaluronate formulated to a viscosity of 40,000±20,000 cps at shear rate of 2 sec⁻¹, 25° C. VISCOAT® viscoelastic solution is relatively unstable at room temperature and its manufacturer recommends that it be stored at 2°-8° C. (36°-46° F.) and warmed to room temperature just prior to use. Also, the ProVisc® viscoelastic solution is a cohesive viscoelastic containing a high molecular weight, non-inflammatory highly purified fraction of sodium hyaluronate, dissolved in physiological sodium chloride phosphate buffer. It is also relatively unstable at room temperature and its manufacturer recommends that it be stored at 2°-8° C. (36°-46° F.) and warmed to room temperature just prior to use. The VISCOAT® viscoelastic solution and the ProVisc® viscoelastic solution are sometimes used and formulated in combination. For example, the DisCoVisc® Ophthalmic Viscosurgical Device (Alcon) is product which combines the VISCOAT® viscoelastic solution and the ProVisc® viscoelastic solution in a single pre-filled syringe and the DuoVisc® Viscoelastic system (Alcon) is a product that provides VISCOAT® viscoelastic solution and the ProVisc® viscoelastic solution in separate pre-filled syringes. Like their individual components, the DisCoVisc® and DuoVisc® products must also be stored at 2°-8° C. (36°-46° F.) and warmed to room temperature just prior to use.

There remains a need in the art for the development of new stabilized glycosaminoglycan materials, such as hyaluronic acid or salts of hyaluronic acid, that are stable when stored at room temperature and which exhibit desirable rheological properties.

SUMMARY OF THE INVENTION

The present invention provides compositions that comprise glycosaminoglycans, such as hyaluronic acid or another hyaluronan, in combination with a stabilizing and/or viscosity increasing agent. The present invention also provides methods for using such compositions.

In accordance with the invention, there are provided compositions that comprise a glycosaminoglycan (e.g., hyaluronic acid or a hyaluronic acid salt) in combination with at least one agent selected from the group consisting of i) polyglycols (e.g., polyethylene glycol), ii) Hydroxy Polyanionic Polysaccharides (e.g., dextran, sodium alginate, alginic acid, propylene glycol alginate, carboxymethyl cellulose and carboxyethyl cellulose, hydroxyl ethyl starch, hydroxyl propyl methyl cellulose, hydroxy propyl ethyl cellulose, hydroxy propyl cellulose, methyl cellulose, polylysine, polyhistidine, polyhydroxy proline, poly ornithine, polyvinyl pyrolidone, polyvinyl alcohol, chitosan, etc.) and iii) long chain Nitrogen containing polymers (e.g., Polylysine, Polyvinylpyrrolidone, and polyvinyl alcohol). Such compositions may be prepared in aqueous solution having a pH of from about 5.0 to about 9.0, preferably pH 7.0-7.4.

In accordance with one embodiment of the invention, a hyaluronan such as hyaluronic acid may be combined with at least one polyglycol in a ratio, and under conditions, which result in the preparation retaining the viscosity and lubricity of the hyaluronan substantially longer than if it had not been combined with the polyglycol. Any suitable hyaluronan like, hyaluronic acid sodium salt and any suitable polyglycol like, polyethylene glycol, including long chain hydroxy polyanionic polysaccharides (e.g., sodium alginate, alginic acid, propylene glycol alginate, carboxymethyl cellulose, carboxyethyl cellulose, etc.), but not polyanionic polysaccharides (e.g., Dextran sulfates), long chain nitrogen containing polymers (e.g., polylysine, polyhistidine, polyhydroxy proline, polyornithine, polyvinylpyrrolidone, etc.), hydroxy polysaccharides (e.g., hydroxyethyl starch, dextran, hydroxypropylmethyl cellulose, Hydroxy Propyl Cellulose, Methyl Cellulose etc.), nitrogen containing hydroxy polysaccharides (e.g., Chitosan, etc.), and polyhydroxy linear polymers (e.g., polyvinyl alcohol, polyhydroxy proline, etc.) may be used, particularly, the long chain hydroxy polyanionic polysaccharides are not only stabilizing the hyaluronan but also increasing viscosity and lubricity of the hyaluronan synergistically. For example, see Example 1. In some cases, the preparation may include other active or inactive ingredients or reactants including, but not limited to, drugs, cosmetics, preservatives, pH adjusting agents, tonicity adjusting agents, thickening or gelling agents, water, coloring agents, fragrance, etc. The stabilized hyaluronan preparations of this invention may be liquid solutions, gels, creams, or any other useable forms. The stabilized hyaluronan preparations of this invention may be used for a variety of medical and non-medical (e.g., household or industrial) applications, including topical administration to the eye (e.g., to moisturize the eye, treat dry eye, promote corneal healing, facilitate reepithelialization for non-infectious corneal erosion, management of dry eye syndrome, allergic conjunctivitis, and contact lens wear, etc.), topical administration (e.g., to moisturize the skin, to treat dry skin or dermatological disorders), lubrication or body tissues or body orifices, lubrication of devices (e.g., catheters, scopes, instruments, etc.), application to tissues during surgery to deter post-surgical adhesion formation, subcutaneous injection for removing wrinkles in addition as vehicles and active drug delivery depot.

Further in accordance with the invention, there are provided methods for manufacturing hyaluronan preparations wherein hyaluronan is combined with a polyglycol. The hyaluronan may be combined with the polyglycol in a ratio and under conditions that result in reaction without chemical structural changes (e.g., chemical conformational changes via complex formation) between the hyaluronan and the polyglycol such that remains stable for an extended period of time (e.g., 2 years or more) at room temperature.

Further aspects, details and embodiments of the present invention will be understood by those of skill in the art upon reading the detailed description and examples set forth here below.

DETAILED DESCRIPTION

Figure 1A:
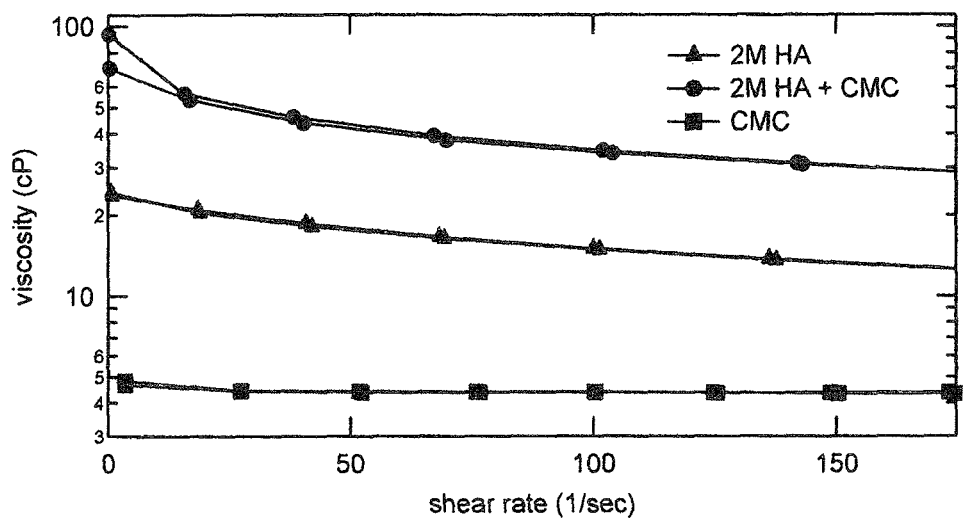
FIG. 1A is a graph of viscosity vs. shear rate for room temperature, pH 5.2 solutions of: 0.5% carboxy methyl cellulose (CMC), 0.15% hyaluronic acid having a molecular weight of 2 million Daltons (2 MDa HA) and 0.15% 2 MDa HA+0.5% CMC.

The following detailed description is intended to describe some, but not necessarily all, examples or embodiments of the invention. No effort has been made to exhaustively describe all possible examples and embodiments of the invention. Thus, the contents of this detailed description shall not limit the scope of the invention in any way.

Polyglycol Stabilized Hyaluronans

In accordance with the present invention, there are provided compositions comprising a hyaluronan combined with a polyglycol, wherein the properties of the hyaluronan (e.g., viscosity and lubricity) are maintained for a prolonged period of time. Thus, polyglycols may be added to or included in various hyaluronan preparations to prolong the shelf stability and usefulness of such preparations.

A polyglycol is defined as a polyhydric alcohol of a monomeric glycol. Polyethylene Glycols (PEGs) are a family of linear, water-soluble polyglycols. PEGs are formed by polymerization of ethylene oxide. The generalized formula for polyethylene glycol is:

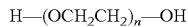

H—(OCH$_2$CH$_2$)$_n$—OH where "n" is the average number of repeating oxyethylene groups.

Using the methods of the present invention, hyaluronan can be complexed with a PEG to form hyaluronan preparations that remain stable at room temperature for extended periods of time (e.g., 2 years or more) without substantial chemical break down of the hyaluronan and resultant change in viscosity and lubricity.

In preparations of the present invention wherein hyaluronan is combined with a polyglycol (e.g., PEG), the polyglycol may preferably have an average molecular weight in the range of about 200 to about 35,000 and more preferably, in at least some applications, an average molecular weight in the range of about 6000 to about 8000.

Also, in preparations of the present invention wherein hyaluronan is combined with a polyglycol (e.g., PEG), the hyaluronan may preferably have an average molecular weight in the range of about 2×10$^3$ to about 5×10$^6$ and more preferably, in at least some applications, an average molecular weight in the range of about 2×10$^5$-3×10$^6$.

Also, in preparations of the present invention wherein hyaluronan is combined with a polyglycol (e.g., PEG), the weight ratio of hyaluronan to polyglycol may be in the range of from about 0.1:1 to about 10:1 and more preferably in at least some applications such weight ratio of hyaluronan to polyglycol may be in the range of from about 1:2 to about 1.10.

Also, in preparations of the present invention wherein hyaluronan is combined with a polyglycol (e.g., PEG) and any other optional components examples of which are set forth in the formulations shown in Examples 1 and 2 below, the concentration of hyaluronan in the preparation may be in the range of about 0.01% by weight to about 10% by weight.

Also, in preparations of the present invention wherein hyaluronan is combined with a polyglycol (e.g., PEG) and any other optional components examples of which are set forth in the formulations shown in Examples 1 and 2 below, the pH of the preparation may be in the range of from about 5.0 to about 9.5 or more preferably in at least some applications, from about 7.0 to about 7.4. Appropriate acidifying and/or alkaline (e.g., buffering) agents may be added in accordance with procedures well known in the art to adjust the pH of the preparation as needed or desired.

Also, in preparations of the present invention wherein hyaluronan is combined with a polyglycol (e.g., PEG) and any other optional components examples of which are set forth in the formulations shown in Examples 1 and 2 below, the tonicity of the preparation may preferably be in the range of about 200 mOsm to about 340 mOsm. Hyperosmolar and/or hypoosmolar agents (e.g., manitol, water, etc.) may be added in accordance with procedures well known in the art to adjust the tonicity of the preparation as needed or desired.

Example 1

A Stabilized Hyaluronan Preparation

In this example, a liquid hyaluronan preparation is prepared by combining and mixing the components of the following formulation at room temperature:

| | |
|---|---|
| Hyaluronic Acid Sodium Salt | 0.15% |
| Polyethyleneglycol (PEG 8000) | 0.50% |
| Boric Acid | 0.20% |
| Sodium Chloride | 0.58% |
| Postassium Chloride | 0.14% |
| Calcium Chloride Dihydrate | 0.02% |
| Magnesium Chloride Hexahydrate | 0.011% |
| Sodium Chorite/Hydrogen Peroxide | 0.06% |
| Purified Water Q.S | to 100 mL. |

This results in a viscous liquid preparation that is suited for a wide variety of medical or non-medical uses, including use as a lubricant or moisturizing agent, for topical administration to the skin, mucous membranes or eyes, or as a carrier for cosmetics, pharmaceuticals or other agents.

Example 2

Stability Comparison

In this example, hyaluronan compositions were prepared under ambient, room temperature conditions according to Formulations I and II, as follows:

| Formula I: | | Formula II: | |
|---|---|---|---|
| Hyaluronic Acid Sodium Salt | 0.15% | Hyaluronic Acid Sodium Salt | 0.15% |
| — | | Polyethyleneglycol (PEG 8000) | 0.5% |
| Boric Acid | 0.2% | Boric Acid | 0.2% |
| Sodium Chloride | 0.58% | Sodium Chloride | 0.58% |
| Postassium Chloride | 0.14% | Postassium Chloride | 0.14% |

-continued

| Formula I: | | Formula II: | |
|---|---|---|---|
| Calcium Chloride Dihydrate | 0.02% | Calcium Chloride Dihydrate | 0.02% |
| Magnesium Chloride Hexahydrate | 0.11% | Magnesium Chloride Hexahydrate | 0.11% |
| Sodium Chorite/Hydrogen Peroxide | 0.06% | Sodium Chorite/Hydrogen Peroxide | 0.06% |
| Purified Water Q.S | to 100 mL. | Purified Water Q.S | to 100 mL. |

Both Formulation I and Formulation 2 provide a lubricious liquid solution as described in Example 1 above. However, when stored at room temperature, the preparation of Formula I looses substantial viscosity and becomes substantially less lubricious within few weeks. In contrast, the preparation of Formula II remains stable and does not undergo any substantial change in viscosity or lubricity for at least two (2) years.

Long Chain Hydroxy Polyanionic Polysaccharide Stabilized Hyaluronans and Other Glycosaminoqlycans Glycosaminoglycans (Including Hyaluronic acid) are important substances in connective tissues in determining the viscoelastic properties of joints and of other structures that are subject to mechanical deformation. Hyaluronic acid is one of the major glycosaminoglycans that occur in many living substances as synovial fluid. Hyaluronic acid is a major component of the extracellular matrix and contributes to cellular migration and proliferation and neuronal morphogenesis. Hyaluronic acid also acts as a lubricant and shock absorber in joints, in the vitreous body of the eye and other parts of the body.

One drawback of administering exogenous hyaluronic acid for therapeutic or other biomedical purposes is that hyaluronic acid degrades very rapidly and consequently loses its viscosity and its lubricity. This limits the many biomedical applications of the hyaluronic acid. Some of the noteworthy therapeutic and other biomedical applications of hyaluronic acid have included its use in tissue grafting, catheter lubrication for insertion into human bodies, scope and endoscope lubrication, skin grafting, dermal wound healing, cell culture, bioengineering and cell bioengineering, eye and joint lubrication, vitreous humor replacement, artificial tears for dry eyes, contact lens storage and wear, corneal wound healing, treatment of allergic conjunctivitis, as a viscoelastic agent in cataract surgery, as an additive in cosmetics and personal care products, as a drug delivery vehicle, etc.

Applicants have discovered that hyaluronic acid can also be stabilized with Long chain hydroxy polyanionic polysaccharides (e.g., sodium alginate, alginic acid, propylene glycol alginate, carboxymethyl cellulose and carboxyethyl cellulose, etc.) in an aqueous solution of pH 5.0-9.0. It has been further discovered that the viscosity of the hyaluronic acid (HA) in aqueous solution at pH 5.0-9.0 can be increased by an order of magnitude or more with the addition of one or more long chain hydroxy polyanionic polysaccharides and such hyaluronic Acid+long chain hydroxy polyanionic polysaccharides possess a non-Newtonian fluid characteristics (shear thinning effects) (see FIG. 1, 2, 3, 4).

Example 3

Comparison of Viscosity Enhancement and Shear Thinning Effects

In this example, the viscosities of various test samples were measured at shear rates ranging from 1-200 1/sec. The compositions of the test samples were as follows:

| Sample | Sample Composition |
|---|---|
| Sample A (1 MDa HA Alone/pH 5.2.) | 0.15 g of 1 MDa Sodium Hyaluronate in 100 mL of the borate buffer solution @ pH 5.2 |
| Sample B (1.5 MDa HA Alone/pH 5.2) | 0.15 g of 1.5 MDa Sodium Hyaluronate in 100 mL of the borate buffer solution @ pH 5.2 |
| Sample C (2 MDa HA Alone/pH 5.2) | 0.15 g of 2 MDa Sodium Hyaluronate in 100 mL of the borate buffer solution @ pH 5.2 |
| Sample D (2 MDa HA Alone/pH 7.2) | 0.15 g of 2 MDa Sodium Hyaluronate in 100 mL of the borate buffer solution @ pH 7.2 |
| Sample E (CMC Alone/pH 5.2) | 0.5 g of CMC in 100 mL of the borate buffer solution @ pH 5.2 |
| Sample F (CMC Alone/pH 7.2) | 0.5 g of CMC in 100 mL of the borate buffer solution @ pH 7.2 |
| Sample G (1 MDa HA + CMC/pH 5.2) | 0.15 g of 1 MDa Sodium Hyaluronate + 0.5 g of CMC in 100 mL of the borate buffer solution 0.15 g of 2 MDa Sodium Hyaluronate in 100 mL of the borate buffer solution @ pH 5.2 |
| Sample H (1.5 MDa HA + CMC/pH 5.2) | 0.15 g of 15M Sodium Hyaluronate + 0.5 g of CMC in 100 mL of the borate buffer solution 0.15 g of 2 MDa Sodium Hyaluronate in 100 mL of the borate buffer solution @ pH 5.2 |
| Sample I (2 MDa HA + CMC/pH 5.2) | 0.15 g of 2 MDa Sodium Hyaluronate + 0.5 g of CMC in 100 mL of the borate buffer solution @ pH 5.2 |
| Sample J (2 MDa HA + CMC/pH 7.2) | 0.15 g of 2 MDa Sodium Hyaluronate + 0.5 g of CMC in 100 mL of the borate buffer solution @ pH 7.2 |
| Sample K (HPMC Alone/pH 7.2) | 0.5 g HPMC in 100 mL of the borate buffer solution @ pH 7.2 |
| Sample L (2 MDa HA + HPMC/pH 7.2) | 0.15 g of 2 MDa Sodium Hyaluronate + 0.5 g of HPMC in 100 mL of the borate buffer solution @ pH 7.2 |
| Sample M (NaALG Alone/pH 7.2) | 0.5 g NaALG in 100 mL of the borate buffer solution @ pH 7.2 |
| Sample N (2 MDa HA + NaALG/pH 7.2) | 0.15 g of 2 MDa Sodium Hyaluronate + 0.5 g of HPMC in 100 mL of the borate buffer solution @ pH 7.2 |
| Sample O (2 MDa HA + Pluronic F127/pH 5.2) | 0.15 g of 2 MDa Sodium Hyaluronate + 0.5 g of Pluronic F127 in 100 mL of the borate buffer solution @ pH 5.2 |
| Sample P (2 MDa HA + PEG/pH 5.2) | 0.15 g of 2 MDa Sodium Hyaluronate + 0.5 g of Pluronic F127 in 100 mL of the borate buffer solution @ pH 5.2 |

Each sample was prepared in a borate buffer solution. The formulation of this borate buffer solution was as follows:

| Component | Amount |
|---|---|
| Boric Acid | 0.20 g |
| Sodium Chloride | 0.58 g |

-continued

| Component | Amount |
|---|---|
| Potassium Chloride | 0.14 g |
| Calcium Chloride Dihydrate | 0.02 g |
| Magnesium Chloride Hexahydrate | 0.011 g |
| Purified Water | Q.S. to 100 mL |

To prepare the buffer, 1 g of boric acid, 2.9 g of Sodium chloride, 0.7 g of potassium chloride, 0.1 g of calcium chloride dihydrate and 0.055 g magnesium chloride hexahydrate were dissolved in distilled water. The solution was diluted to 500 mL. The pH of this buffer solution was adjusted to either 5.2 or 7.2 at room temperature, as indicated.

To insure samples were thoroughly dissolved and well mixed, stock solutions of the polymers in borate buffer were prepared when possible. For hyaluronic acids, 2% stock solutions were used. All stock solutions were vortex mixed and then placed on a shaker until clear and homogeneous.

Hyaluronic acid samples (0.15% HA) were prepared by diluting approximately 0.75 g of the HA stock solution to 10 g using the borate buffer. Again, samples were vortex mixed and placed in a shaker until the solutions were clear and homogeneous.

Viscosity measurements were performed on an AR 1000 rheometer (TA Instruments) using a cone and plate geometry. The cone was 6 cm in diameter with an angle of 1 degree and a truncation gap of 29 mm. The range of torques applied was adjusted to cover shear rates ranging (at minimum) from 25 $sec^{-1}$ to 160 $sec^{-1}$. Shear rates were first increased and then during the experiment. A new sample was loaded for each experiment.

FIG. 1A is a graph showing viscosity vs. shear rate for samples C, E and I. As shown, at pH 5.2, the viscosity of Sample I (2 MDa HA+CMC) was synergistically increased over the viscosity of Samples C (2 MDa HA alone) and E (CMC alone).

Figure 1B:
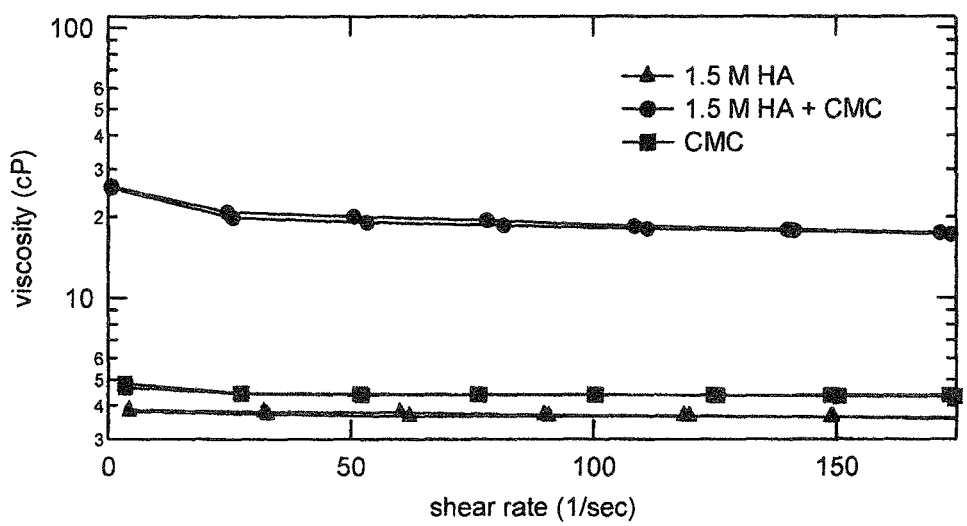
FIG. 1B is a graph of viscosity vs. shear rate for room temperature, pH 5.2 solutions of: 0.5% carboxy methyl cellulose (CMC) alone, 0.15% hyaluronic acid having a molecular weight of 1.5 million Daltons (1.5 MDa HA) alone and 0.15% 1.5 MDa HA+0.5% CMC.

FIG. 1B is a graph showing viscosity vs. shear rate for samples B, E and H. As shown, at pH 5.2, the viscosity of Sample H (1.5 MDa HA+CMC) was synergistically increased over the viscosity of Samples B (1.5 MDa HA alone) and E (CMC alone).

Figure 1C:
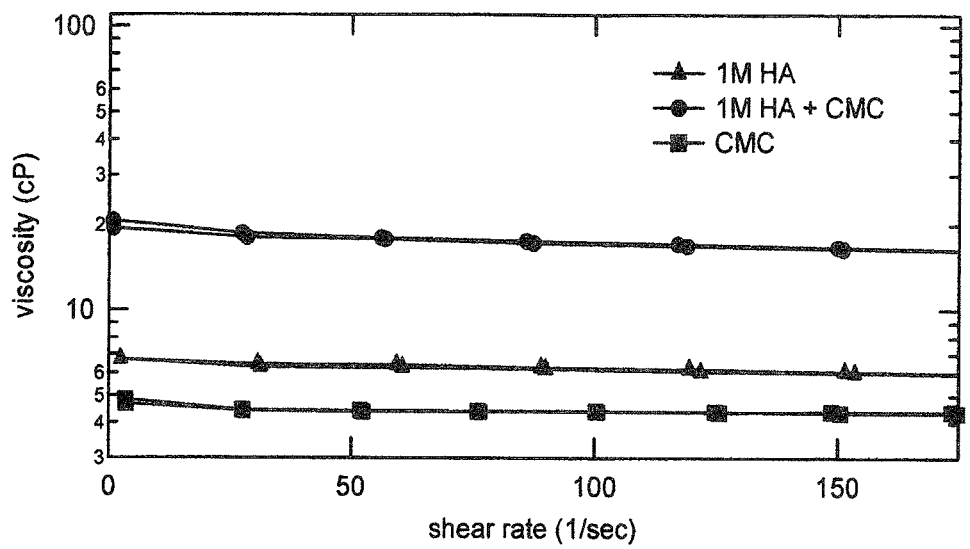
FIG. 1C is a graph of viscosity vs. shear rate for room temperature, pH 5.2 solutions of: 0.5% carboxy methyl cellulose (CMC) alone, 0.15% hyaluronic acid having a molecular weight of 1 million Daltons (1 MDa HA) alone and 0.15% 1 MDa HA+0.5% CMC.

FIG. 1C is a graph showing viscosity vs. shear rate for samples A, E and G. As shown, at pH 5.2, the viscosity of Sample G (1 MDa HA+CMC) was synergistically increased over the viscosity of Samples A (1 MDa HA alone) and E (CMC alone).

Also, when FIGS. 1A-1C are viewed in comparison, it is apparent that the viscosity enhancing effect of CMC was most pronounced in the sample containing 2 MDa HA (Sample K) and least pronounced in the sample containing 1 MDa HA (Sample G). Thus, the viscosity enhancing effect of CMC is greater with higher molecular weight HA.

Figure 2:
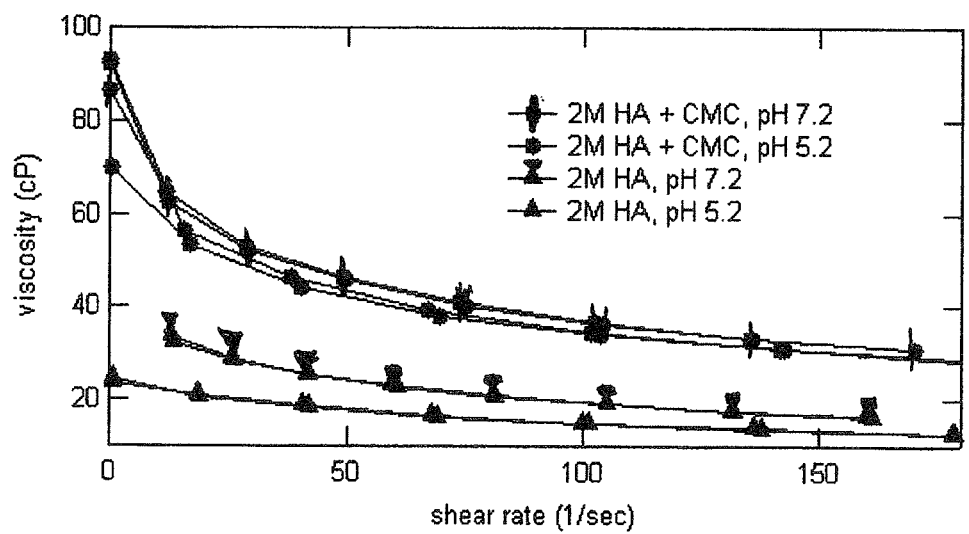
FIG. 2 is a graph of viscosity vs. shear rate for room temperature solutions of: 0.15% 2 MDa HA+0.5% CMC @ pH 7.2, 0.15% 2 MDa HA+0.5% CMC @ pH 5.2, 0.15% 2 MDa HA @ pH 7.2 and 0.15% 2 MDa HA @ pH 5.2.

FIG. 2 is a graph showing viscosity vs. shear rate for samples C, D, I and J. The viscosities of samples D (2 MDa HA alone at neutral pH 7.2) and J (2 MDa HA+CMC at neutral pH 7.2) were greater than the viscosities of samples C (2 MDa HA alone at alkaline pH 5.2) and I (2 MDa HA+CMC at alkaline pH 5.2). Thus, the viscosity of HA, whether alone or in combination with CMC, increases as pH changes from alkaline (5.2) to neutral (7.2).

Figure 3:
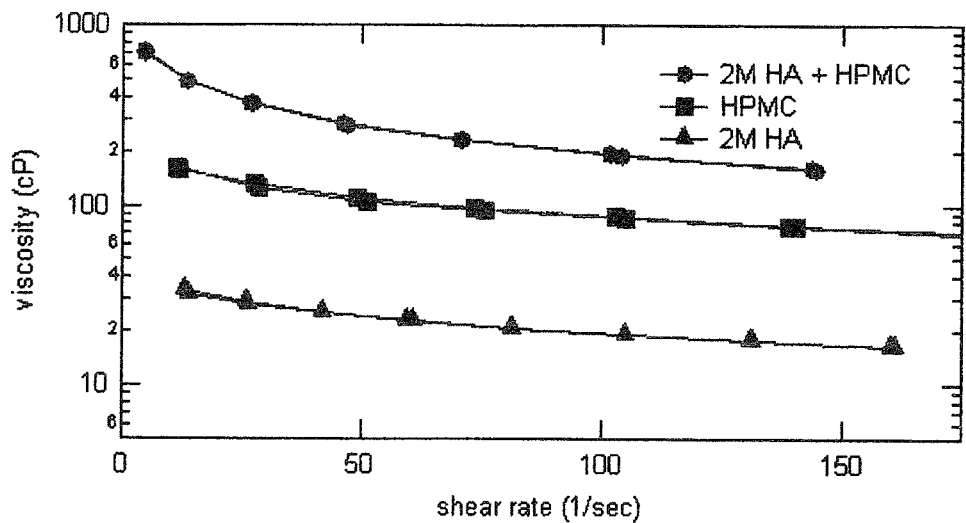
FIG. 3 is a graph of viscosity vs. shear rate for 25° C., pH 7.2 solutions of: 0.15% 2 MDa HA+0.5% hydroxy propyl methyl cellulose (HPMC), 0.5% HPMC and 0.15% 2 MDa HA.

FIG. 3 is a graph showing viscosity vs. shear rate for samples D, K and L. These data indicate that at pH 7.4, the viscosity of Sample L (2 MDa HA+HPMC) was synergistically increased over the viscosities of Samples D (2 MDa HA alone) and K (HPMC alone). Thus, the addition of 0.5% HPMC caused a supraadditive (e.g., synergistic) increase in viscosity of the HA.

Figure 4:
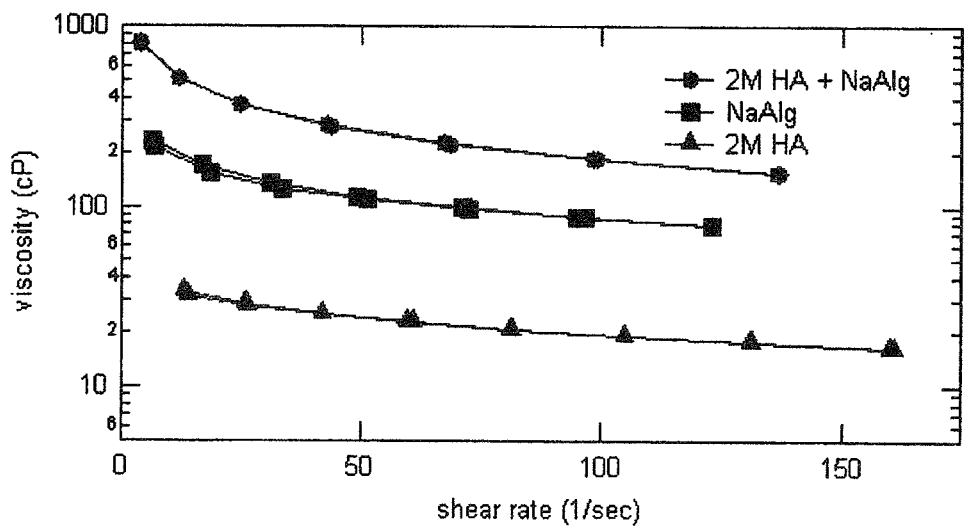
FIG. 4 is a graph of viscosity vs. shear rate for 25° C., pH 7.2 solutions of: 0.15% 2 MDa HA+0.5% sodium alginate (NaALG), 0.5% NaALG and 0.15% 2 MDa HA.

FIG. 4 is a graph showing viscosity vs. shear rate for samples D, M and N. These data indicate that, at pH 7.4, the viscosity of Sample N (2 MDa HA+NaALG) was synergistically increased over the viscosities of Samples D (2 MDa HA alone) and M (Na-ALG alone). Thus, the addition of 0.5% Na-ALG caused a supraadditive (e.g., synergistic) increase in viscosity of the HA.

Figure 5:
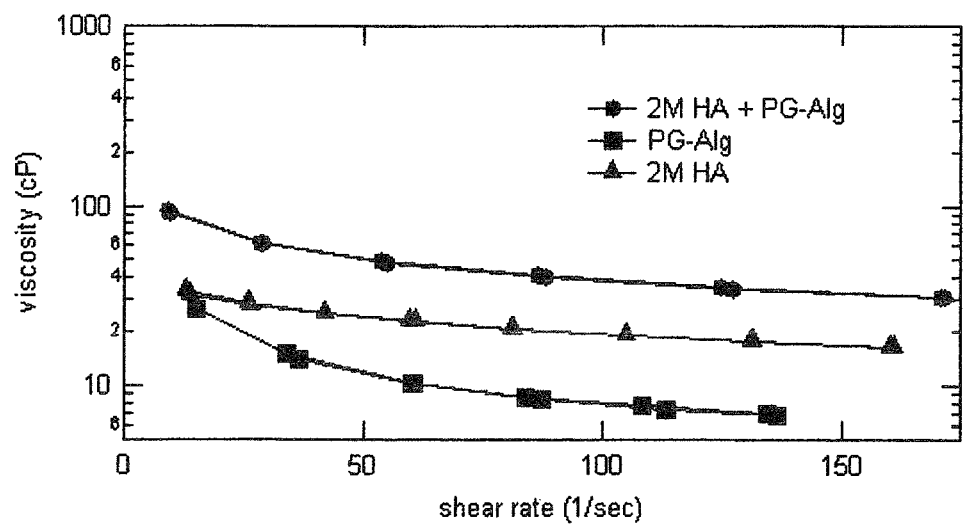
FIG. 5 is a graph of viscosity vs. shear rate for 25° C., pH 7.2 solutions of: 0.15% 2 MDa HA+0.5% propylene glycol alginate (PG-ALG), 0.5% PG-ALG and 0.15% 2 MDa HA.

FIG. 5 is a graph showing viscosity vs. shear rate for samples D, N and O. These data indicate that, at pH 7.4, the viscosity of Sample O (2 MDa HA+PG-ALG) was synergistically increased over the viscosities of Samples D (2 MDa HA alone) and N (PG-ALG alone). Thus, the addition of 0.5% PG-ALG caused a supraadditive (e.g., synergistic) increase in viscosity of the HA.

Figure 6:
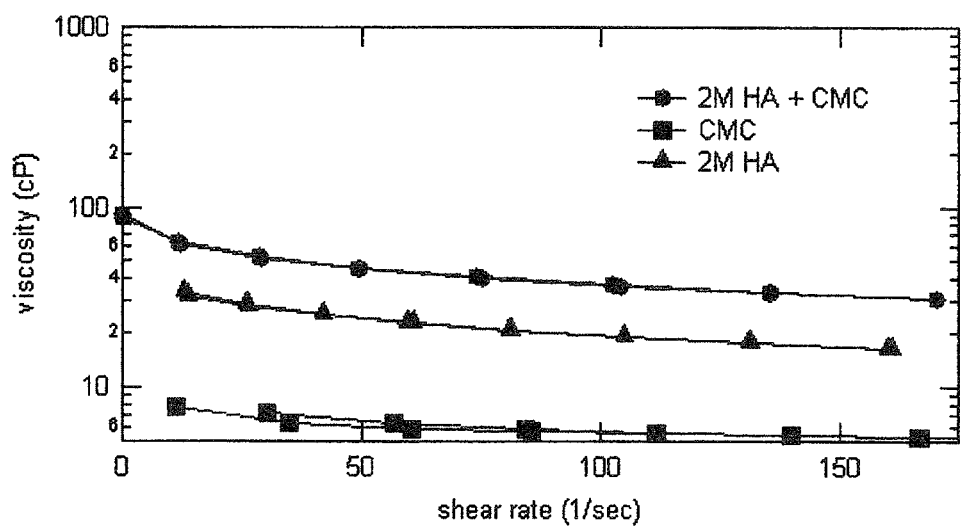
FIG. 6 is a graph of viscosity vs. shear rate for 25° C., pH 7.2 solutions of: 0.15% 2 MDa HA+0.5% CMC, 0.5% CMC and 0.15% 2 MDa HA.

FIG. 6 is a graph showing viscosity vs. shear rate for samples D, F and J. These data indicate that, at pH 7.4, the viscosity of Sample J (2 MDa HA+CMC) was synergistically increased over the viscosities of Samples D (2 MDa HA alone) and F (CMC alone). Thus, the addition of 0.5% CMC caused a supraadditive (e.g., synergistic) increase in viscosity of the HA.

In the following table, the shear thinning grade ratio (STG ratio) was calculated as the ratio of the viscosity at 160 $sec^{-1}$ to the viscosity at 40 $sec^{-1}$ at 30° C., pH 5.2. The following table

| Sample | STG Ratio |
|---|---|
| Sample C (2 MDa HA Alone/pH 5.2) | 1.42 |
| Sample I (2 MDa HA + CMC/pH 5.2) | 1.50 |
| Sample P (2 MDa HA + PEG/pH 5.2) | 1.53 |
| Sample O (2 MDa HA + Pluronic F127/pH 5.2) | 1.45 |

Pluronic F-127 is a registered trademark of BASF Corporation, Florham Park, N.J. It is a difunctional block copolymer surfactant terminating in primary hydroxyl groups also known as Poloxamer 407.

As seen in the table above, at pH 5.2, the STG ratio is greater when 2 MDa HA is combined CMC or PEG than for 2 MDa HA alone or in combination with a stabilizing amount of Pluronic F127. For example, an aqueous gel containing 30% CMC (a stabilizer) contained in a syringe fitted with a 29 gauge needle cannot be injected through the 29 gauge needle at room temperature (or may be forced through that needle only with great difficulty). However, the addition of 0.15 g HA (0.15%) into the CMC gel makes the gel become much thinner when a mechanical force is applied on it due to the shear thinning effects. Accordingly, the HA+CMC gel may be injected through the 29 gauge needle easily using a standard syringe and standard injection technique. This shear thinning property of the gel is of great value in preparations that are intended to be injected through needles or otherwise passed through small diameter lumens, passageways or openings. Examples of specific applications where these shear thinning effects will be of value will be in glycosaminoglycan gels (e.g., HA gels) and other preparations intended for use as substance delivery depots/carriers or dermal/tissue fillers.

Accordingly, the hyaluronic acid/long chain hydroxy polyanionic polysaccharides system becomes thinner as a mechanical force is applied on it. Thus, it can be ideally used as an injectable formulation alone (e.g., as a viscoelastic agent or tissue filler/bulking agent) or may be combined with diagnostic or therapeutic agents (e.g., as a drug deliver carrier/depot) such that the diagnostic or therapeutic agents are then released kinetically.

Glycosaminoglycans, like hyaluronic acid, are made up of disaccharide repeating units containing a derivative of an amino sugar, either glucosamine or galactosamine in which one of the sugars has a negatively charged carboxylate or sulfate. Thus, glycosaminoglycans can be stabilized by the long chain hydroxyl polyanionic polysaccharides. Some major glycosaminoglycans are Dermatan Sulfate, Karatan Sulfate, Chondroitin 6-Sulfate and Heparin.

Glucosaminoglycans, like hyaluronic acid, are made up of disaccharide repeating units containing a derivative of an amino sugar, either glucosamine or galactosamine in which one of the sugars has a negatively charged carboxylate or sulfate group. Thus, Aginic acid, Polyethylene glycol alginate, CMC, etc. can also stabilize the glycosaminoglycans.

The term glycosaminoglycan as used herein includes but is not limited to hyaluronans, dermatan sulfate, keratan sulfate, chondroitin 6-sulphate and heparin.

In addition the stabilization of the above mentioned glycosaminoglycans can be performed using Carboxyethyl Cellulose as well as many other Carboxymethyl and Carboxyethyl cellulose compounds.

In summary, the combination of hyaluronic acid with a long chain hydroxyl polyanionic polysaccharides (e.g., Alginic acid, sodium alginate, Propylene glycol alginate, dextran, CMC, etc.) results in a composition having unique properties, including but not limited to:

1. Addition of the Long Chain Hydroxy Polyanionic Polysaccharides stabilizes the unstable Hyaluronic acid (Glycosaminoglycans)
2. Addition of the Long Chain Hydroxy Polyanionic Polysaccharides increases the viscosity of Hyaluronic Acid synergically in aqueous solution at pH 5.0-9.0 by an order of magnitude-, or more.
3. Addition of the Long Chain Hydroxy Polyanionic Polysaccharides enhances the shear thinning effects where the enhancement is pronouncedly higher with a higher molar mass of Hyaluronic Acid.
4. Addition of the hydroxy polysaccharides as well as nitrogen containing hydroxyl polysaccharides and long chain nitrogen containing polymers.
5. Polyhydroxy linear polymers.

The following are non-limiting examples of formulations of the present invention.

FORMULATION EXAMPLES

| Formulation 1 | |
|---|---|
| Sodium Hyaluronate | 0.001%-50.0% |
| Sodium Alginate | 0.001%-50.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

| Formulation 2 | |
|---|---|
| Sodium Hyaluronate | 0.001%-50.0% |
| Alginic Acid | 0.001%-50.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

| Formulation 3 | |
|---|---|
| Sodium Hyaluronate | 0.001%-50.0% |
| Carboxymethylcellulose | 0.005%-40.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

| Formulation 4 | |
|---|---|
| Sodium Hyaluronate | 0.001%-50.0% |
| Propylene Glycol Alginate | 0.001%-50.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

| Formulation 5 | |
|---|---|
| Sodium Hyaluronate | 0.001%-50.0% |
| Hydroxy propyl methyl cellulose | 0.001%-50.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

| Formulation 6 | |
|---|---|
| Sodium Hyaluronate | 0.001%-50.0% |
| Sodium Alginate | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 7 | |
|---|---|
| Sodium Hyaluronate | 0.001%-50.0% |
| Alginic Acid | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 8 | |
|---|---|
| Sodium Hyaluronate | 0.001%-50.0% |
| Propylene Glycol alginate | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 9 | |
|---|---|
| Sodium Hyaluronate | 0.001%-50.0% |
| Carboxymethylcellulose | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 10 | |
|---|---|
| Sodium Hyaluronate | 0.001%-50.0% |
| Hydroxy propyl methyl cellulose | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 11 | |
|---|---|
| Sodium Hyaluronate | 0.15%-3.0% |
| Sodium Alginate | 0.50%-15.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 12 | |
|---|---|
| Sodium Hyaluronate | 0.15%-3.0% |
| Alginic Acid | 0.50%-15.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 13 | |
|---|---|
| Sodium Hyaluronate | 0.15%-3.0% |
| Propylene Glycol Alginate | 0.50%-15.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 14 | |
|---|---|
| Sodium Hyaluronate | 0.15%-3.0% |
| Carboxymethylcellulose | 0.50%-15.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 15 | |
|---|---|
| Sodium Hyaluronate | 0.15%-3.0% |
| Hydroxy propyl methyl cellulose | 0.50%-15.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 16 | |
|---|---|
| Sodium Chondroitin Sulfate | 0.001%-50.0% |
| Alginic Acid | 0.001%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 17 | |
|---|---|
| Sodium Chondroitin Sulfate | 0.001%-50.0% |
| Sodium alginate | 0.001%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 18 | |
| --- | --- |
| Sodium Chondroitin Sulfate | 0.001%-50.0% |
| Propylene Glycol alginate | 0.001%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 19 | |
| --- | --- |
| Sodium Chondroitin Sulfate | 0.001%-50.0% |
| Hydroxy propyl methyl cellulose | 0.001%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 20 | |
| --- | --- |
| Sodium Hyaluronate | 0.001%-50.0% |
| Dextran | 0.005%-40.0% |
| Sodium Phosphate Monobasic, monohydrate | 0.01%-0.1% |
| Sodium Phosphate Dibasic, anhydrous | 0.02-1.0% |
| Sodium Chloride | 0.01%-1.0% |
| HCl or NaOH | Adjust pH to 7.2 |
| Purified water, USP | Q.S. to 100 mL |

| Formulation 21 | |
| --- | --- |
| Sodium Hyaluronate | 0.001%-50.0% |
| Dextran | 0.005%-50.0% |
| Boric Acid | 0.01%-1.0% |
| Sodium Chloride | 0.1%-10.0% |
| Potassium Chloride | 0.01%-10.0% |
| Calcium Chloride dehydrate | 0.001%-10.0% |
| Magnesium Chloride hexahydrate | 0.001%-1.0% |
| HCl or NaOH | Adjust pH to 7.2 |
| Purified water, USP | Q.S. to 100 mL |

The invention has been described here above with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for filling or bulking tissue in a human or animal subject, said method comprising the step of introducing into the tissue a filling or bulking amount of a viscous composition that comprises i) a first component selected from the group consisting of hyaluronans and ii) a second component selected from the group consisting of alginic acid and alginates, wherein the second component is present in an amount which a) increases the viscosity of the preparation by at least one order of magnitude, b) increases shelf stability of the hyaluronan and c) causes the viscosity of the composition to decrease when subjected to a shear force.

2. A method according to claim 1 wherein the composition is injected into the tissue.

3. A method according to claim 2 wherein the composition is injected through a hollow needle, cannula or other lumen.

4. A method according to claim 3 wherein the composition has a shear thinning grade ratio of 1.50 or greater.

5. A method according to claim 4 wherein the hollow needle, cannula or other lumen comprises a hypotube or needle of 29 gage or smaller.

6. A method according to claim 1 wherein the composition is injected as a dermal filler to fill wrinkles, lines or folds in the skin.

7. A preparation for topical application to the skin, said preparation comprising hyaluronic acid and sodium alginate, said preparation having a pH of about 5 to about 9.5, wherein the sodium alginate is present in an amount which a) increases the viscosity of the preparation by at least one order of magnitude, b) increases shelf stability of the hyaluronic acid and c) causes the viscosity of the solution to decrease when subjected to a shear force.

8. A preparation according to claim 7 wherein the hyaluronic acid has an average molecular weight in the range of about $2 \times 10^3$ to about $5 \times 10^6$.

9. A preparation according to claim 7 wherein the hyaluronic acid has an average molecular weight in the range of about $2 \times 10^5$ to about $3 \times 10^6$.

10. A preparation according to claim 7 wherein the weight ratio of hyaluronic acid to sodium alginate is from about 0.1:1 to about 10:1.

11. A preparation according to claim 7 wherein the weight ratio of hyaluronic acid to sodium alginate is from about 1:2 to about 1:10.

12. A preparation according to claim 7 wherein the concentration of hyaluronic acid is in the range of from about 0.01% by weight to about 10% by weight.

13. A preparation according to claim 7 having a pH in the range of about 5.0 to about 9.5.

14. A preparation according to claim 7 having a pH of about 7.2-7.4.

15. A preparation according to claim 7 further comprising a therapeutic substance.

16. A preparation according to claim 7 further comprising a cosmetic substance.

17. A method according to claim 1 wherein the first component comprises hyaluronic acid.

18. A method according to claim 1 wherein the first component comprises a salt of hyaluronic acid.

19. A method according to claim 1 wherein the first component comprises hyaluronic acid sodium salt.

20. A method according to claim 1 wherein the second component comprises alginic acid.

21. A method according to claim 1 wherein the second component comprises sodium alginate.

22. A method according to claim 1 wherein the second component comprises propylene glycol alginate.

* * * * *